United States Patent
Gharda et al.

(10) Patent No.: US 12,221,421 B2
(45) Date of Patent: Feb. 11, 2025

(54) PROCESS FOR SYNTHESIS OF FIPRONIL

(71) Applicant: Gharda Chemicals Limited, Maharashtra (IN)

(72) Inventors: Keki Hormusji Gharda, Maharashtra (IN); Diwakar Shenoy, Maharashtra (IN); Laxminarayan Shet, Maharashtra (IN); Yatin Samangadkar, Maharashtra (IN); Abhijeet Suresh Kawade, Maharashtra (IN)

(73) Assignee: GHARDA CHEMICALS LIMITED, Maharashtra (IN)

( * ) Notice: Subject to any disclaimer, the term of this patent is extended or adjusted under 35 U.S.C. 154(b) by 695 days.

(21) Appl. No.: 17/439,870

(22) PCT Filed: Feb. 24, 2020

(86) PCT No.: PCT/IB2020/051532
§ 371 (c)(1),
(2) Date: Sep. 16, 2021

(87) PCT Pub. No.: WO2020/188376
PCT Pub. Date: Sep. 24, 2020

(65) Prior Publication Data
US 2022/0185783 A1    Jun. 16, 2022

(30) Foreign Application Priority Data
Mar. 19, 2019    (IN) .............................. 201921010712

(51) Int. Cl.
*C07D 231/44*    (2006.01)
(52) U.S. Cl.
CPC ................................ *C07D 231/44* (2013.01)
(58) Field of Classification Search
CPC .................................................... C07D 231/44
USPC ..................................................... 548/367.4
See application file for complete search history.

(56) References Cited

U.S. PATENT DOCUMENTS

| 7,777,052 B2 | 8/2010 | Gharda et al. |
| 2011/0034530 A1 | 2/2011 | Yang et al. |
| 2012/0309806 A1 | 12/2012 | Sukopp et al. |

OTHER PUBLICATIONS

Aldrich, Catalog Handbook of Fine Chemicals, 1998-1999, p. 225 & 323 . . . (3 pages. (Year: 1998).*
Int'l Search Report and Written Opinion issued Jul. 7, 2020 in Int'l Application No. PCT/IB2020/051532.
Saeed et al, "Recent synthetic approaches to fipronil, a super-effective and safe pesticide," Research on Chemical Intermediates, vol. 42, No. 9, pp. 6805-6813 (2016).

* cited by examiner

*Primary Examiner* — Taylor V Oh
(74) *Attorney, Agent, or Firm* — Panitch Schwarze Belisario & Nadel LLP

(57) ABSTRACT

A process for the synthesis of fipronil, which is a broad spectrum insecticide of the following chemical structure, is provided.

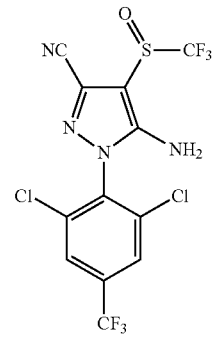

The process provides fipronil with a yield in the range of 75% to 90% and purity in the range of 95% to 97%. By the process, the observed amount of sulfone impurity i.e., 5-amino-1-(2,6-dichloro-4-trifluoromethylphenyl)-3-cyano-4-trifluoro methylsulfonyl pyrazole in fipronil is in the range of 0% to 0.5%.

18 Claims, No Drawings

PROCESS FOR SYNTHESIS OF FIPRONIL

CROSS-REFERENCE TO RELATED APPLICATIONS

This application is a Section 371 of International Application No. PCT/IB2020/051532, filed Feb. 24, 2020, which was published in the English language on Sep. 24, 2020, under International Publication No. WO 2020/188376 A1, which claims priority under 35 U.S.C. § 119 (b) to Indian application No. 201921010712, filed Mar. 19, 2019, the disclosure of each of which is incorporated herein by reference in their entireties.

FIELD

The present disclosure relates to a process for the synthesis of Fipronil.

BACKGROUND

The background information herein below relates to the present disclosure but is not necessarily prior art.

Fipronil is a broad-spectrum insecticide and it belongs to 1-phenylpyrazole class of insecticides.

Fipronil is characterized by high efficiency, low toxicity, and especially, low residue.

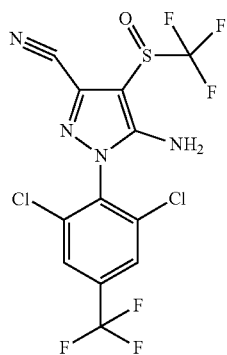 [SMILES: N#Cc1nn(-c2c(Cl)cc(C(F)(F)F)cc2Cl)c(N)c1S(=O)C(F)(F)F]

IUPAC name: (R.S)-5-Amino-1-[2,6-dichloro-4-(trifluoromethyl)phenyl]-4-(trifluoromethylsulfinyl) pyrazole-3-carbonitrile CAS number: 120068-37-3

A commercial process involves oxidation in the final step of the synthesis of fipronil wherein, the sulfinyl precursor of Fipronil is oxidized using a suitable oxidizing agent. However, during the oxidation process some amount of fipronil (so obtained product) undergoes further oxidation, thereby resulting in the formation of corresponding sulfone compound 5-amino-1-[2,6-dichloro-4-(trifluoromethyl)phenyl]-4-[(trifluoromethyl)sulfonyl]-1H-pyrazole-3-carbonitrile, as an impurity. Therefore, the aforementioned commercial route provides fipronil with a low purity. Further, the sulfone impurity is difficult to separate from fipronil.

Another commercial process for the synthesis of fipronil involves trifluoromethanesulfinylation of corresponding aryl-pyrazole intermediate using trifluoromethanesulfinyl chloride [CAS no. 20621-29-8]. Unfortunately, hitherto known processes for preparing trifluoromethanesulfinyl chloride are complex, and provide trifluoromethanesulfinyl chloride with a low purity and with low yield. Further, the trifluoromethanesulfinyl chloride may contain corresponding sulfone impurity such as trifluoromethanesulfonyl chloride that can lead to the formation of sulfone impurity (5-amino-1-[2,6-dichloro-4-(trifluoromethyl)phenyl]-4-[(trifluoromethyl)sulfonyl]-1H-pyrazole-3-carbonitrile) during the synthesis of fipronil.

Thus, there is felt a need for developing a simple process for preparing Fipronil which results in a high yield, with high purity.

OBJECTS

Some of the objects of the present disclosure, which at least one embodiment herein satisfies, are as follows.

It is an object of the present disclosure to ameliorate one or more problems of the prior art or to at least provide a useful alternative.

An object of the present disclosure is to provide a process for the synthesis of fipronil in a high yield, and with high purity.

Another object of the present disclosure is to provide a simple and efficient process for the synthesis of fipronil.

Other objects and advantages of the present disclosure will be more apparent from the following description, which is not intended to limit the scope of the present disclosure.

SUMMARY

The present disclosure provides a process for the synthesis of fipronil. The process comprises reacting 5-Amino-3-cyano-1-(2,6-dichloro-4-trifluoro methyl phenyl)-pyrazole with trifluoromethane sulfinyl chloride and amine hydrochloride, in the halogenated organic fluid medium to obtain a reaction mixture. The reaction mixture is cooled to a temperature in the range of 20° C. to 35° C. to obtain a cooled reaction mixture. A mixture of the halogenated organic fluid medium and water is added to the cooled reaction mixture to obtain an admixture. The so obtained admixture is neutralized with a neutralizing agent to obtain a biphasic mixture containing an organic phase and an aqueous phase. The organic phase comprising fipronil is separated and cooled to a temperature in the range of 2° C. to 30° C. to obtain a precipitate of fipronil. The so obtained precipitate is filtered, washed, and dried under vacuum to obtain fipronil with purity in the range of 95% to 97%. The reaction of 5-Amino-3-cyano-1-(2,6-dichloro-4-trifluoro methyl phenyl)-pyrazole with trifluoromethane sulfinyl chloride and amine hydrochloride is carried out at a temperature in the range of 40° C. to 80° C. for a time period in the range of 2 hours to 8 hours. In accordance with the embodiments of the present disclosure, fipronil is obtained with a yield in the range of 75% to 90%. In accordance with the present disclosure, amine hydrochloride is selected from the group consisting of diethylamine hydrochloride, N, N, N', N'-tetraethyl ethan-1,2-diamine dihydrochloride and their amine sulphate salt.

DETAILED DESCRIPTION

Embodiments are provided so as to thoroughly and fully convey the scope of the present disclosure to the person skilled in the art. Numerous details are set forth, relating to specific components, and methods, to provide a complete understanding of the embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

As used herein, the term "and/or" includes any and all combinations of one or more of the associated listed elements.

The terms first, second, third, etc., should not be construed to limit the scope of the present disclosure as the aforementioned terms may be only used to distinguish one element, component, region, layer or section from another component, region, layer or section. Terms such as first, second, third etc., when used herein do not imply a specific sequence or order unless clearly suggested by the present disclosure.

Fipronil is a broad-spectrum insecticide. Conventional processes for the synthesis of fipronil are complex, and provide fipronil of low purity. Further, the fipronil obtained by the conventional processes may contain corresponding sulfone compound 5-amino-1-[2,6-dichloro-4-(trifluoromethyl)phenyl]-4-[(trifluoro methyl)sulfonyl]-1H-pyrazole-3-carbonitrile, as an impurity, which is difficult to separate from fipronil.

The present disclosure envisages a simple process for preparing fipronil in a high yield and with high purity. Further, it is desired that the synthesized fipronil contains less than 0.5%, more preferably negligible amount of sulfone impurity i.e., 5-amino-1-[2,6-dichloro-4-(trifluoromethyl)phenyl]-4-[(trifluoromethyl) sulfonyl]-1H pyrazole-3carbonitrile.

In one aspect, the present disclosure provides a process for synthesis of fipronil.

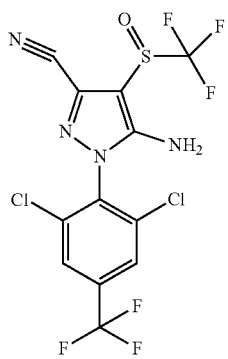 [SMILES: N#Cc1nn(-c2c(Cl)cc(C(F)(F)F)cc2Cl)c(N)c1S(=O)C(F)(F)F]

The process of the present disclosure is represented herein below as Scheme-1.

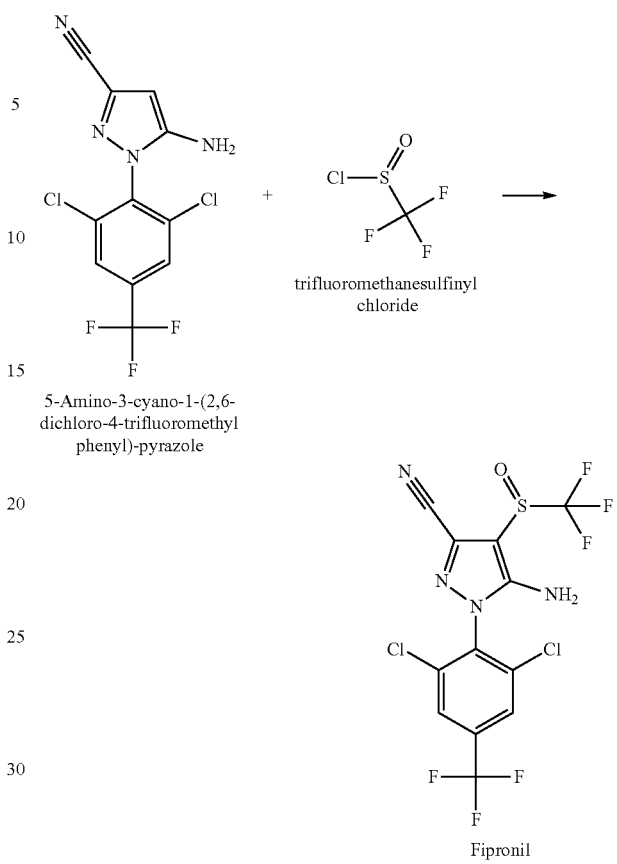

The process of the present disclosure is described in detail.

In accordance with the process of the present disclosure, 5-Amino-3-cyano-1-(2,6-dichloro-4-trifluoromethylphenyl)-pyrazole is reacted with trifluoromethane sulfinyl chloride and amine hydrochloride in the halogenated organic fluid medium to obtain a reaction mixture.

In accordance with the embodiments of the present disclosure, the halogenated organic fluid medium is at least one selected from the group consisting of dichloromethane, dichloroethane, dibromoethane, chlorobromomethane, chloroform, carbon tetrachloride, chlorobenzene, dichlorobenzene & bromobenzene.

In an embodiment, the amine hydrochloride is selected from the group consisting of diethylamine hydrochloride, N, N, N', N'-tetraethyl ethan-1,2-diamine dihydrochloride and their amine sulphate salt.

The reaction of 5-Amino-3-cyano-1-(2,6-dichloro-4-trifluoro methyl phenyl)-pyrazole with trifluoromethane sulfinyl chloride and amine hydrochloride is carried out at a temperature in the range of 40° C. to 80° C. In an embodiment, the reaction is carried out at a temperature in the range of 48-55° C.

The reaction of 5-Amino-3-cyano-1-(2,6-dichloro-4-trifluoro methyl phenyl)-pyrazole with trifluoromethane sulfinyl chloride and amine hydrochloride is carried out for a time period in the range of 2 hours to 8 hours. In an embodiment, the reaction time period is 5 hours.

In accordance with the embodiments of the present disclosure, the molar ratio of trifluoromethane sulfinyl chloride to 5-amino-3-cyano-1-(2,6-dichloro-4-trifluoromethylphenyl)-pyrazole is in the range of 1:1 to 2:1. In an exemplary embodiment, the molar ratio of trifluoromethyl sulfinyl chloride to 5-amino-3-cyano-1-(2,6-dichloro-4-trifluoromethylphenyl)-pyrazole is in the range of 1.1:1 to 1.2:1.

The purity of trifluoromethyl sulfinyl chloride used in the process of the present disclosure can be in the range of 95% to 99.9%. Further, trifluoromethyl sulfinyl chloride comprises sulfone impurity trifluoromethanesulfonyl chloride in the range of 0 to 0.5%

The molar ratio of amine hydrochloride to 5-amino-3-cyano-1-(2,6-dichloro-4-trifluoromethylphenyl)-pyrazole is in the range of 1:1 to 3:1. In an exemplary embodiment of the present disclosure, the molar ratio of diethylamine hydrochloride to 5-amino-3-cyano-1-(2,6-dichloro-4-trifluoromethylphenyl)-pyrazole is in the range of 1.5:1.0 to 2.5:1

The reaction mixture is cooled at a temperature in the range of 20° C. to 35° C. to obtain a cooled reaction mixture. A mixture of the halogenated organic fluid medium and water is added to the cooled reaction mixture to obtain an admixture. The so obtained admixture is neutralized with a neutralizing agent to obtain a biphasic mixture containing an organic phase and an aqueous phase. The organic phase comprising fipronil is separated and cooled to a temperature in the range of 2° C. to 30° C. to obtain a precipitate of fipronil. The so obtained precipitate is filtered, washed, and dried under vacuum to obtain fipronil with purity in the range of 95% to 97%.

The neutralizing agent is at least one selected from the group consisting of an aqueous ammonia solution, aqueous NaOH solution, aqueous KOH solution, $Na_2CO_3$ solution, $NaHCO_3$ solution and an aqueous $CaCl_2$ solution.

In accordance with the embodiments of the present disclosure, fipronil is obtained with a yield in the range of 75% to 90%.

In accordance with the embodiments of the present disclosure, the amount of sulfone impurity 5-amino-1-(2,6-dichloro-4-trifluoromethylphenyl)-3-cyano-4-trifluoromethylsulfonylpyrazole in fipronil obtained by the process of the present disclosure is in the range of 0% to 0.5%.

In accordance with the embodiments of the present disclosure, amine hydrochloride and the halogenated organic fluid medium are recovered from the aqueous phase. The recovered amine hydrochloride can be reused in the process of preparation of fipronil.

In accordance with one embodiment of the present disclosure, fipronil is recrystallized using the halogenated organic fluid medium.

The halogenated organic fluid medium used for recrystallization of fipronil can be further recovered and reused.

The process of the present application further comprises addition of Boric acid and $CaCl_2$ as hydrofluoric acid binders prior to neutralization. The addition of Boric acid and $CaCl_2$ protects hydrofluoric acid attack on glass reactor.

The process of the present is disclosure is simple, and efficient, and provides fipronil in a high yield, and with a high purity. The process of the present disclosure is carried out using a low amount of the halogenated fluid medium. The halogenated fluid medium used in the process step is carried forward in the distillation step. The used halogenated organic fluid medium is recovered and the recovered halogenated organic fluid medium is reused. Therefore, the process of the present disclosure is environment friendly.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAILS

Preparation of Fipronil in Accordance with the Process of the Present Disclosure:

Example-I 500 ml dry ethylene dichloride was charged in 1-lit vertical reactor equipped with stirrer, thermometer pocket, and condenser with scrubber. 321 gm of 5-amino-1-[2,6-dichloro-4-(trifluoro methyl) phenyl]-1H-pyrazole-3-carbonitrile, 1.0 gm Boric acid, 2.0 gm $CaCl_2$ and 197.1 gm of diethyl amine hydrochloride (dry powder) was added in the ethylene dichloride with stirring and heated to 50° C. under stirring to obtain a mixture. 175.3 gm of trifluoro methyl sulfinyl chloride was added to the mixture with stirring at 50° C. for 5 hours to obtain a reaction mixture. The so obtained reaction mixture was cooled to 25° C. to obtain a cooled reaction mixture. 3000 ml of ethylene dichloride and 400 ml of water ($H_2O$) was added in the cooled reaction mixture to obtain an admixture. The admixture was neutralized by using an aqueous ammonia solution (8-10N) till pH 7 to obtain a neutralized admixture. After neutralization, the neutralized admixture was heated to 65° C. to obtain a biphasic mixture containing bottom organic layer and top aqueous layer. The bottom organic layer was separated and cooled to 5° C. to obtain precipitate. The so obtained precipitated was filtered, washed twice with the ethylene dichloride to minimize impurities in Fipronil mass. The Fipronil mass was dried under vacuum and then dried at 100° C. to get 335 gm (Yield=76.66%) of fipronil having purity of 96%.

Example-II 600 ml dry ethylene dichloride was charged in 1-lit vertical reactor equipped with stirrer, thermometer pocket, and condenser with scrubber. 321 gm of 5-amino-1-[2,6-dichloro-4-(trifluoro methyl) phenyl]-1H-pyrazole-3-carbonitrile, 1.0 gm Boric acid, 2.0 gm $CaCl_2$ and 219 gm of diethyl amine hydrochloride (dry powder) was added in the ethylene dichloride with stirring and then heated to 45° C. with stirring to obtain a mixture. 175.3 gm of trifluoro methyl sulfinyl chloride was added to the mixture at 45° C. with stirring for 5 hours to obtain a reaction mixture. The so obtained reaction mixture was cooled to 25° C. to obtain a cooled reaction mixture. 2900 ml of ethylene dichloride and 400 ml of water ($H_2O$) was added to the cooled reaction mixture to obtain an admixture. The admixture was neutralized by using an aqueous ammonia solution (8-10N) till pH 7 to obtain a neutralized admixture. After neutralization, the neutralized admixture was heated to 70° C. to obtain a biphasic mixture containing bottom organic layer and top aqueous layer. The bottom organic layer was separated and cooled to 5° C. to obtain precipitate. The so obtained precipitate was filtered, washed twice with the ethylene dichloride. The filtered fipronil mass was dried under vacuum and then dried at 100° C. to get 338 gm (Yield=77.34%) of fipronil with purity=96.4%.

Example-III 500 ml dry ethylene dichloride was charged in 1-lit vertical reactor equipped with stirrer, thermometer pocket, and condenser with scrubber. 321 gm of 5-amino-1-[2,6-dichloro-4-(trifluoro methyl) phenyl]-1H-pyrazole-3-carbonitrile, 1.0 gm Boric acid, 2.0 gm $CaCl_2$ and 164.25 gm of diethyl amine hydrochloride (dry powder) was added in ethylene dichloride with stirring and heated to 60° C. with stirring to obtain a mixture. 175.3 gm of trifluoro methyl sulfinyl chloride was added in the mixture with stirring and stirred for 5 hours at 60° C. to obtain a reaction mixture. The so obtained reaction mixture was cooled to 20° C. to obtain a cooled reaction mixture. 3000 ml of ethylene dichloride and 400 ml of water ($H_2O$) was added to the cooled reaction mixture to obtain admixture. The admixture is neutralized by using an aqueous ammonia solution (8-10N) till pH 7 to obtain a neutralized admixture. The neutralized admixture was heated to 65° C. to obtain a biphasic mixture containing bottom organic layer and top aqueous layer. The bottom organic layer was separated and cooled to 3° C. to obtain precipitate. The so obtained precipitate was filtered, washed twice with the ethylene dichloride. The filtered Fipronil mass was dried under vacuum and then dried at 110° C. to get 330 gm (Yield=75.51%) of fipronil with purity=95.8%.

Example-IV 500 ml dry ethylene dichloride was charged in 1-lit vertical reactor equipped with stirrer, thermometer pocket, and condenser with scrubber. 321 gm of 5-amino-1-[2,6-dichloro-4-(trifluoro methyl) phenyl]-1H-pyrazole-3-carbonitrile, 1.0 gm Boric acid, 2.0 gm $CaCl_2$ and 219 gm of diethyl amine hydrochloride (dry powder) was added in ethylene dichloride with stirring and heated to 50° C. with stirring to obtain a mixture. 175.3 gm of trifluoro methyl sulfinyl chloride was added to the mixture under stirring and heated for 5 hours at 50° C. to obtain a reaction mixture. The so obtained reaction mixture was cooled to 25° C. to obtain cooled reaction mixture. 3000 ml of ethylene dichloride and 400 ml of water ($H_2O$) was added to the cooled reaction mixture to obtain an admixture. The admixture is neutralized by using an aqueous ammonia solution (8-10N) till pH 7 to obtain a neutralized admixture. The so obtained neutralized admixture was heated to 70° C. to obtain a biphasic mixture containing bottom organic layer and top aqueous layer. The bottom organic layer was separated and concentrated to adjust the level of ethylene dichloride to 800 ml by recovering 2700 ml ethylene dichloride at 85° C. followed by cooling to 20° C. to obtain precipitate. The so obtained precipitated was filtered, washed twice with the dichloroethane. The solid mass was dried under vacuum and then dried at 110° C. to get 360 gm (Yield=82.38%) of fipronil with purity=96.5%.

Example-V 600 ml dry ethylene dichloride was charged in 1-lit vertical reactor equipped with stirrer, thermometer pocket, and condenser with scrubber. 321 gm of 5-amino-1-[2,6-dichloro-4-(trifluoro methyl) phenyl]-1H-pyrazole-3-carbonitrile, 1.0 gm Boric acid, 2.0 gm $CaCl_2$ and 273.75 gm of diethyl amine hydrochloride (dry powder) was added in ethylene dichloride with stirring and heated to 50° C. to obtain a mixture. To the mixture 183 gm of trifluoro methyl sulfinyl chloride was added under stirring and heated at 50° C. for 5 hours to obtain a reaction mixture. The so obtained reaction mixture was cooled to 25° C. to obtain a cooled reaction mixture. To the reaction mixture, 2900 ml of ethylene dichloride and 400 ml of water ($H_2O$) was added to obtain an admixture. The admixture was neutralized by using an aqueous ammonia solution (8-10N) till pH get 7 to obtain a neutralized admixture. The neutralized admixture was heated to 70° C. to obtain a biphasic mixture containing bottom organic layer and top aqueous layer. The bottom organic layer was separated and concentrated to adjust the level of ethylene dichloride to 800 ml by recovering 2700 ml ethylene dichloride at 85° C. followed by cooling to 20° C. to obtain precipitate. The so obtained precipitated was filtered, washed twice with the chlorinated solvent to obtain a cake. The cake was dried under vacuum and then dried at 100° C. to get 375 gm (Yield=85.81%) of fipronil with purity of 96.3%.

Example-VI 600 ml dry ethylene dichloride was charged in 1-lit vertical reactor equipped with stirrer, thermometer pocket, and condenser with scrubber. 321 gm of 5-amino-1-[2,6-dichloro-4-(trifluoro methyl) phenyl]-1H-pyrazole-3-carbonitrile, 1.0 gm Boric acid, 2.0 gm $CaCl_2$ and 490 gm of N, N, N', N'-tetraethyl ethan-1,2-diamine dihydrochloride (dry powder), was added in ethylene dichloride with stirring and heated at 50° C. with stirring to obtain a mixture. 183 gm of trifluoro methyl sulfinyl chloride was added to the mixture under stirring for 5 hours at 50° C. to obtain a reaction mixture. The so obtained reaction mixture was cooled to 25° C. to obtain a cooled reaction mixture. To the reaction mixture, 2900 ml of ethylene dichloride and 400 ml of water ($H_2O$) was added to obtain an admixture. The admixture was neutralized by using an aqueous ammonia solution (8-10N) till get the pH 7 to obtain a neutralized admixture. The neutralized admixture was heated to 70° C. to obtain a biphasic mixture containing bottom organic layer and top aqueous layer. The bottom organic layer was separated and concentrated to adjust the level of ethylene dichloride to 800 ml by recovering 2700 ml ethylene dichloride at 85° C. followed by cooling to 20° C. to obtain precipitate. The so obtained precipitated was filtered, washed twice with the dichloroethane solvent to obtain a Fipronil solid mass. The Fipronil solid mass was dried under vacuum and then dried at 90° C. to get 345 gm (Yield=78.95%) of fipronil with purity=95.5%.

Example-VII 600 ml dry ethylene dichloride was charged in 1-lit vertical reactor equipped with stirrer, thermometer pocket, and condenser with scrubber. 321 gm of 5-amino-1-[2,6-dichloro-4-(trifluoro methyl) phenyl]-1H-pyrazole-3-carbonitrile, 1.0 gm Boric acid, 2.0 gm $CaCl_2$ and 273.75 gm of diethyl amine hydrochloride (dry powder), was added in ethylene dichloride with stirring and heated to 50° C. with stirring to obtain a mixture. 183 gm of trifluoro methyl sulfinyl chloride was added the mixture with stirring and stirred for 5 hours at 50° C. to obtain a reaction mixture. The so obtained reaction mixture was cooled to 25° C. to obtain a cooled reaction mixture. To the reaction mixture, 2900 ml of ethylene dichloride and 400 ml of water ($H_2O$) was added to obtain an admixture. The admixture was neutralized by using an aqueous ammonia solution (8-10N) till pH 7 to obtain a neutralized admixture. The neutralized admixture was heated to 70° C. to obtain a biphasic mixture containing bottom organic layer and top aqueous layer. The bottom organic layer was separated and concentrated to recover 3500 ml ethylene dichloride at 85-90° C. and then to the concentrated mass added 1000 ml of monochlorobenzene followed by cooling to 20° C. to obtain precipitate. The so obtained precipitated was filtered, washed twice with monochlorobenzene the to obtain a Fipronil solid mass. The Fipronil solid mass was dried under vacuum and then dried at 115° C. to get 375 gm (Yield=85.81%) of fipronil with purity=97%.

Example-VIII 500 ml dry ethylene dichloride was charged in 1-lit vertical reactor equipped with stirrer, thermometer pocket, and condenser with scrubber. 321 gm of 5-amino-1-[2,6-dichloro-4-(trifluoro methyl) phenyl]-1H-pyrazole-3-carbonitrile, 1.0 gm Boric acid, 2.0 gm $CaCl_2$ and 219 gm of diethyl amine hydrochloride (dry powder) was added in ethylene dichloride with stirring and heated to 50° C. with stirring to obtain a mixture. 175.3 gm of trifluoro methyl sulfinyl chloride was added to the mixture under stirring and heated for 5 hours at 50° C. to obtain a reaction mixture. The reaction mixture was drowned into 3000 ml of ethylene dichloride and 1000 ml of 10.0% W/V $CaCl_2$ solution at 30° C. to obtain an admixture. The so obtained neutralized admixture was heated to 70° C. to obtain a biphasic mixture containing bottom organic layer and top aqueous layer. The bottom organic layer was separated and neutralized by using an aqueous ammonia solution (0.5-1.0N) till pH 7 to obtain a neutralized admixture. The so obtained neutralized admixture was heated to 70° C. to obtain a biphasic mixture containing bottom organic layer and top aqueous layer. The bottom organic layer was separated and concentrated to adjust the level of ethylene dichloride to 800 ml by recovering 2700 ml ethylene dichloride at 85° C. followed by cooling to 20° C. to obtain precipitate. The so obtained precipitated was filtered, washed twice with the dichloroethane. The solid mass was dried under vacuum and then dried at 110° C. to get 380 gm (Yield=87.00%) of fipronil with purity=96.5%.

To achieve the yield of Fipronil greater than 85%, the catalyst (diethylamine hydrochloride) quantity should be minimum 219 grams per mole of batch size and drowning of the reaction mass in $CaCl_2$ solution gives better yield in comparison to other examples. Diethyl amine hydrochloride is preferably better catalyst than the other amine hydrochloride.

Technical Advances and Economical Significance

The present disclosure described herein above has several technical advantages including, but not limited to, the realization of a process that:
is simple and efficient;
provides fipronil in high yield with high purity; and
is environmentally friendly.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation

The invention claimed is:
1. A process for the synthesis of fipronil, the process comprising the following steps:
   a) reacting trifluoromethane sulfinyl chloride with 5-amino-3-cyano-1-(2,6-dichloro-4-trifluoromethylphenyl)-pyrazole and amine hydrochloride in a halogenated fluid medium to obtain a reaction mixture;
   b) cooling said reaction mixture to a temperature in the range of 20° C. to 35° C. to obtain a cooled reaction mixture;
   c) adding a mixture of said halogenated fluid medium and water to said cooled reaction mixture to obtain an admixture;
   d) neutralizing said admixture with a neutralizing agent to obtain a biphasic mixture containing an organic phase and an aqueous phase;
   e) separating said organic phase comprising fipronil followed by cooling said separated organic phase to a temperature in the range of 2° C. to 30° C. to obtain a precipitate of fipronil; and
   f) filtering said precipitate to obtain a solid, washing said solid and drying said washed solid to obtain fipronil with purity in the range of 95% to 97%;
   wherein the amount of 5-amino-1-(2,6-dichloro-4-trifluoromethylphenyl)-3-cyano-4-trifluoromethylsulfonyl pyrazole in the fipronil is in the range of 0% to 0.5%.
2. The process as claimed in claim 1, wherein fipronil is obtained with a yield in the range of 75% to 90%.
3. The process as claimed in claim 1, wherein said step a) is carried out at a temperature in the range of 40° C. to 80° C.
4. The process as claimed in claim 1, wherein said step a) is carried out for a time period in the range of 2 hours to 8 hours.
5. The process as claimed in claim 1, wherein the halogenated fluid medium is selected from the group consisting of dichloromethane, dichloroethane, dibromoethane, chlorobromomethane, chloroform, carbon tetrachloride, chlorobenzene, dichlorobenzene, and bromobenzene.

6. The process as claimed in claim 1, wherein the molar ratio of trifluoromethane sulfinyl chloride to 5-amino-3-cyano-1-(2,6-dichloro-4-trifluoromethylphenyl)-pyrazole is in the range of 1:1 to 2:1.

7. The process as claimed in claim 1, wherein the purity of said trifluoromethane sulfinyl chloride is in the range of 95% to 99.9%.

8. The process as claimed in claim 1, wherein the molar ratio of amine hydrochloride to 5-amino-3-cyano-1-(2,6-dichloro-4-trifluoromethylphenyl)-pyrazole is in the range of 1:1 to 3:1.

9. The process as claimed in claim 1, wherein said neutralizing agent is at least one selected from the group consisting of water, aqueous ammonia solution, aqueous NaOH solution, aqueous KOH solution, $Na_2CO_3$ solution, $NaHCO_3$ solution and aqueous $CaCl_2$) solution.

10. The process as claimed in claim 1, wherein amine hydrochloride, water, and the halogenated fluid medium are recovered from said aqueous phase.

11. The process as claimed in claim 1, wherein said amine hydrochloride is selected from the group consisting of diethylamine hydrochloride, N, N, N', N'-tetraethyl ethan-1,2-diamine dihydrochloride and amine sulphate salt.

12. The process as claimed in claim 1, wherein Boric acid and $CaCl_2$) are added as a hydrofluoric acid binders prior to neutralization.

13. The process as claimed in claim 1, wherein in step (d) the neutralized admixture is heated at a temperature in the range of 65° C. to 70° C. to obtain said biphasic mixture containing said organic phase and said aqueous phase.

14. The process as claimed in claim 1, wherein in step (f) said washing is carried out with a halogenated fluid medium.

15. The process as claimed in claim 1, wherein in step (f) said drying comprises drying under vacuum and further drying at a temperature in the range of 90° C. to 115° C.

16. The process as claimed in claim 1, wherein said process comprises the following sub-steps:
   i. drowning said admixture obtained in step (c) in a neutralizing agent to obtain a neutralized admixture;
   ii. heating said neutralized admixture to obtain a biphasic mixture containing a bottom organic layer and a top aqueous layer; and
   iii. separating said bottom organic layer, and using said bottom organic layer in said step (d).

17. The process as claimed in claim 16, wherein said neutralizing agent is aqueous $CaCl_2$) solution.

18. The process as claimed in claim 16, wherein in step (ii) said heating is carried out at a temperature in the range of 65° C. to 70° C.

* * * * *